United States Patent [19]

Farrell

[11] Patent Number: 4,549,996
[45] Date of Patent: Oct. 29, 1985

[54] PERFUME DISPENSER

[75] Inventor: Geoffrey Farrell, Crewe, England

[73] Assignee: Burroughs Wellcome Co., Research Triangle Park, N.C.

[21] Appl. No.: 653,502

[22] Filed: Nov. 19, 1984

Related U.S. Application Data

[62] Division of Ser. No. 376,168, May 7, 1982, Pat. No. 4,499,012.

[30] Foreign Application Priority Data

May 8, 1981 [GB] United Kingdom ............ 8114055
Sep. 28, 1981 [GB] United Kingdom ............ 8129168

[51] Int. Cl.$^4$ ............................................. C11B 9/00
[52] U.S. Cl. .................................. 261/19; 261/94; 252/522 A
[58] Field of Search ............... 261/19, 94; 522/552 A

[56] References Cited

U.S. PATENT DOCUMENTS

| | | | |
|---|---|---|---|
| 1,715,252 | 5/1929 | Sperr, Jr. ............... | 261/94 |
| 3,796,657 | 3/1974 | Pretorius et al. ....... | 261/94 |
| 3,993,444 | 11/1976 | Brown .................... | 261/94 |
| 4,297,233 | 10/1981 | Gualandi ................ | 252/522 A |

FOREIGN PATENT DOCUMENTS

| | | | |
|---|---|---|---|
| 65244 | 11/1982 | European Pat. Off. ...... | 252/522 A |
| 69840 | 6/1978 | Japan ........................ | 252/522 A |
| 115762 | 10/1978 | Japan ........................ | 252/522 A |
| 78965 | 6/1980 | Japan ........................ | 252/522 A |

OTHER PUBLICATIONS

Kirk-Othmer, "Encyclopedia of Chemical Technology", vol. 5, 2 Ed. (1964), pp. 541–557, 580–581.

Primary Examiner—Tim Miles
Attorney, Agent, or Firm—Donald Brown

[57] ABSTRACT

Known perfume dispensing materials such as those which comprise paper or ceramics have been found to affect adversely the odor of the perfume they dispense. Vermiculite appears to overcome this disadvantage when used in a perfume dispensing material.

4 Claims, No Drawings

PERFUME DISPENSER

This is a division of application Ser. No. 376,168 filed 05/07/82, now U.S. Pat. No. 4,449,012.

This invention relates to perfume dispensing material suitable for use in imparting a pleasant odour into the atmosphere. The material could typically be used in any household room or in an office or in a domestic, industrial or public wash room or lavatory.

Known perfume dispensing materials comprise paper and a gel, each incorporating a perfume to be dispensed. U.S. Pat. No. 3,945,950 discloses such a gel based on diethylene glycol ethers. It has now been found that vermiculite can form a suitable vehicle for a perfume to be dispensed.

Vermiculite is a form of expanded mica and is a hydrated magnesium-aluminium-iron silicate. It has previously been used as a catalyst, as loose fill insulation, as a filler, as packing material, in cat litter and as part of a floor sweeping composition. U.S. Pat. No. 3,921,581 discloses the use of vermiculite and other solid materials in cat litter. Although a perfume agent is present in trace to minor quantities (typically 0.05 to 5% by weight), it will be appreciated that the solid material, of which vermiculite is only one example, is present in cat litter chiefly for the purpose of absorbing unpleasant odours. It thus serves quite a different purpose from the vermiculite in the present invention. A typical analysis of Montana vermiculite ore is as follows:

| | |
|---|---|
| $SiO_2$ | 38.64% |
| $MgO$ | 22.68% |
| $Al_2O_3$ | 14.94% |
| $Fe_2O_3$ | 9.29% |
| $K_2O$ | 7.84% |
| $CaO$ | 1.23% |
| $Cr_2O_3$ | 0.29% |
| $Mn_3O_4$ | 0.11% |
| $Cl$ | 0.28% |

According to a first aspect of the present invention, there is provided perfume dispensing material comprising a block, or granules having a granule size of over 1000 microns, of vermiculite impregnated with one or more perfume oils, at least 10% of the weight of the material being perfume oil. As used herein, the term "perfume oil" means a pure or formulated perfume oil. Such oils typically have relative densities (specific gravities) of between 0.8 and and 1.1. Other ingredients may be present in the dispensing material.

The vermiculite may be in the form of a block (which could include a binder such as a resin) or in the form of granules, conveniently in having a granule size of between 3,000 and 6,000 microns. It is to be understood that, when granules are described as having a granule size of over a given amount, the mean diameters of substantially all, but not necessarily absolutely all, the granules are over that given amount. Typically, 90, 95 or even 99% of the so described granules may have been mean diameters above that given amount. Preferably, the weight of vermiculite in the material is approximately the same as the weight of perfume oil(s) in the material, but 15, 20, 25, 30, 35, 40, 45, 50, 55, 60, 65, 70 or 75% by weight of the composition may be perfume oil. It is preferred that the composition should not be wet, as the free flow characteristics of a dry composition may be useful in a manufacturing process for impregnation and packing of vermiculite.

The material may be placed in a container, and, therefore, according to a second aspect of the invention, there is provided a perfume dispenser comprising a container containing perfume dispensing material in accordance with the first aspect of the invention. The container is inert and may be an open plastics material container. The dispenser may comprise a fan to increase the rate of diffusion of perfume from the material.

It has been found that the inert vermiculite appears to enhance the rate of perfume diffusion and allows the perfume oil or oils to diffuse by means of their own vapour pressure from the material without any adverse effects on fragrance quality. Known perfume carriers do not always possess these properties. For example, paper and ceramics seem to affect the odour of perfume over a period of time probably because of a chromatographic effect by means of which light oils diffuse off first.

For a better understanding of the present invention, and to show how it may be put into effect, the following Examples will now be given.

EXAMPLE 1

Vermiculite (25 g) was impregnated with 40 g concentrated perfume oils (30–40 ml) by admixture. Approximately 50% of the perfume dispensing material thus formed was perfume oil. The material was placed in an open plastics material container, from which the perfume could readily diffuse, in a room of 1500 cubic feet capacity and was replaced after 8 weeks.

EXAMPLE 2

Vermiculite (20 g) was impregnated with a perfume oil (30 g) having the following composition:

| | % |
|---|---|
| Acetophenone | 0.300 |
| Cedarwood Oil | 30.000 |
| Cedarwood Ketone | 4.000 |
| Cinnamic Aldehyde | 0.500 |
| Clove Leaf Oil | 6.000 |
| Coumarin | 2.000 |
| Diphenyl Methane | 5.000 |
| Ethyl Vanillin | 0.700 |
| Musk Ambrette | 2.000 |
| Musk Xylol | 4.000 |
| Olibanum Resinoide | 4.000 |
| Para Tertiary Butyl Cyclohexyl Acetate | 6.000 |
| Patchouli | 4.000 |
| Rosette 20035 | 10.000 |
| Styrax Resinoide | 6.600 |
| Terpineol | 10.000 |
| Tolu Resinoide | 5.000 |
| | 100.000 |

The impregnated material was placed in a squat high density polythene container of approximately 200 ml capacity. The contents of the container were well shaken to ensure uniform and complete dispersion of the perfume in the vermiculite. The container was placed under a small battery operated centrifugal fan to assist diffusion of perfume from the material. The material kept fresh a room of 1800 cubic feet capacity for 6 weeks.

EXAMPLE 3

Vermiculite (20 g) was impregnated with a perfume oil (30 g) having the following composition:

| | |
|---|---:|
| Amyl Salicylate | 10.000 |
| Cedarwood Oil | 12.500 |
| Diphenyl Methane | 4.000 |
| Dihydro Myrcenol | 4.000 |
| Eugenol | 2.000 |
| Jasmin Base | 12.500 |
| Musk Ambrette | 1.000 |
| Methyl Anthranilate | 5.000 |
| Methyl Cinnamate | 3.000 |
| Methyl Naphthyl Ketone | 1.000 |
| Nerolin Bromelia | 8.000 |
| Oilbanum Resinoide | 4.000 |
| Phenylacetaldehyde 50% in Phenyl Ethyl Alcohol | 2.700 |
| Phenyl Ethyl Alcohol | 5.000 |
| Roselium | .300 |
| Rosette 20035 | 10.000 |
| Terpineol | 10.000 |
| Ylang Ether | 5.000 |
| | 100.000 |

The impregnated material was used in the same manner as that in Example 2 and had a similar effect.

I claim:

1. A perfume dispenser comprising an inert container containing a perfume dispensing material wherein the material comprises granules having a granule size of over 1000 microns, of vermiculite impregnated, with one or more perfume oils, at least 10% of the weight of the material being perfume oil.

2. A dispenser according to claim 1 wherein the dispenser includes a fan to enhance the rate of displasion of perfume from the material.

3. A dispenser according to claim 1, wherein the container is open and made of plastics material.

4. A dispenser according to claim 3 wherein the dispenser includes a fan to enhance the rate of diffusion of perfume from the material.

* * * * *